(12) United States Patent
Jensen et al.

(10) Patent No.: US 7,985,540 B2
(45) Date of Patent: *Jul. 26, 2011

(54) METHOD, CHIP, DEVICE AND SYSTEM FOR EXTRACTION OF BIOLOGICAL MATERIALS

(75) Inventors: Gert Bolander Jensen, Copenhagen (DK); Lars Thomsen, Ålborg (DK); Oene Robert Veltman, Ålborg (DK)

(73) Assignee: Delta, Dansk Elektronik, Lys & Akustik, Hørsholm (DK)

( * ) Notice: Subject to any disclaimer, the term of this patent is extended or adjusted under 35 U.S.C. 154(b) by 111 days.

This patent is subject to a terminal disclaimer.

(21) Appl. No.: 10/590,630

(22) PCT Filed: Feb. 25, 2005

(86) PCT No.: PCT/DK2005/000132
§ 371 (c)(1), (2), (4) Date: Nov. 16, 2007

(87) PCT Pub. No.: WO2005/083078
PCT Pub. Date: Sep. 9, 2005

(65) Prior Publication Data
US 2008/0108119 A1    May 8, 2008

(30) Foreign Application Priority Data

Feb. 26, 2004  (DK) ................................ 2004 00305

(51) Int. Cl.
*C12Q 1/68* (2006.01)
*C12P 19/34* (2006.01)
(52) U.S. Cl. ........................... 435/6; 435/91.1; 435/91.2
(58) Field of Classification Search .................. None
See application file for complete search history.

(56) References Cited

U.S. PATENT DOCUMENTS

| | | | |
|---|---|---|---|
| 342,548 A | 5/1886 | Walker | |
| 895,729 A | 8/1908 | Cottrell | |
| 1,204,907 A | 11/1916 | Schmidt | |
| 1,250,088 A | 12/1917 | Burns | |
| 1,605,648 A | 11/1926 | Cooke | |
| 1,931,436 A | 10/1933 | Deutsch | |
| 2,085,349 A | 6/1937 | Wintermute | |
| 2,129,783 A | 9/1938 | Penney | |
| 2,142,129 A | 1/1939 | Hoss et al. | |
| 2,297,601 A | 9/1942 | Williams | |
| 2,847,082 A | 8/1958 | Roos | |
| 3,910,779 A | 10/1975 | Penney | |
| 3,999,964 A | 12/1976 | Carr | |
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 4,970,154 A | 11/1990 | Chang | |
| 5,674,742 A | 10/1997 | Northrup et al. | |
| 5,723,591 A | 3/1998 | Livak et al. | |
| 5,891,694 A | 4/1999 | Arisawa et al. | |
| 5,989,824 A * | 11/1999 | Birmingham et al. | ............ 435/6 |
| 6,126,800 A | 10/2000 | Caillat et al. | |
| 6,364,941 B2 | 4/2002 | Liu et al. | |
| 6,511,831 B1 | 1/2003 | Bernhagen et al. | |
| 6,586,253 B1 | 7/2003 | Harrison et al. | |
| 6,623,544 B1 | 9/2003 | Kaura | |
| 6,673,621 B1 | 1/2004 | Mitchell | |
| 2001/0029793 A1 | 10/2001 | Moler et al. | |
| 2002/0017195 A1 | 2/2002 | Tolvanen | |
| 2002/0115201 A1 | 8/2002 | Barenburg et al. | |
| 2003/0136205 A1 | 7/2003 | Totoki | |
| 2003/0146100 A1 | 8/2003 | Huang et al. | |

FOREIGN PATENT DOCUMENTS

| | | |
|---|---|---|
| DE | 2756164 A1 | 6/1979 |
| EP | 1481083 B1 | 12/2004 |
| GB | 2 329 633 A | 3/1999 |
| WO | WO 89/03426 A2 | 4/1989 |
| WO | WO 97/08293 A1 | 3/1997 |
| WO | WO 99/28742 A1 | 6/1999 |
| WO | WO 99/38612 A1 | 8/1999 |
| WO | WO 99/57314 A1 | 11/1999 |
| WO | WO 00/26405 A1 | 5/2000 |
| WO | WO 01/19963 A2 | 3/2001 |
| WO | WO03004996 A2 | 1/2003 |
| WO | WO03031067 A1 | 4/2003 |
| WO | WO03074731 A2 | 9/2003 |
| WO | W02004009840 A1 | 1/2004 |
| WO | WO 2004/013329 A1 | 2/2004 |

OTHER PUBLICATIONS

Atrih, et al. 2001. Analysis of the role of bacterial endospore cortex structure in resistance properties and demonstration of its conservation amongst species. *Journal of Applied Microbiology*, 91:364-372.
Boe, et al. 1989. Replication origins of single-stranded-DNA plasmid pUB110. *Journal of Bacteriology*, 171(6):3366-3372.
Cano, et al. 1995. Revival and identification of bacterial spores in 25- to 40-million-year-old Dominican amber. *Science*, 268:1060-1064.

(Continued)

*Primary Examiner* — Young J Kim
(74) *Attorney, Agent, or Firm* — Peter B. Scull; K Kalan; Berenbaum Weinshienk PC

(57) ABSTRACT

The present invention relates to a method, a chip, a device and a system for extraction of biological material form biological cells. The invention involves exposing the biological particles to an alternating electric field in a sample chamber and may also involve subsequent analysis of the biological material after the extraction.

14 Claims, 6 Drawing Sheets

OTHER PUBLICATIONS

Chen, et al. 2000. Analysis of DNA fragments by microchip electrophoresis fabricated on poly(methylmethacrylate) substrates using a wire-imprinting method. *Electrophoresis*, 21:165-170.

Cho, et al. 1999. Kinetics of inactivation of *Bacillus subtilis* spores by continuous or intermittent Ohmic and conventional heating. *Biotechnology and Bioengineering*, 62(3):368-372.

Cserhalmi, et al. 2002. Inactivation of *Saccharomyces cerevisiae* and *Bacillus cereus* by pulsed electric fields technology. *Innovative Food Science & Emerging Technologies*, 3:41-45.

Daniel, et al. 1998. Silicon microchambers for DNA amplification. *Sensors and Actuators A*, 71:81-88.

Dull, et al. 2002. *Bacillus anthracis* aerosolization associated with a contaminated mail sorting machine. *Emerging Infectious Diseases*, 8(10):1044-1047.

Fridez, et al. 1996. PCR DNA typing of stamps: Evaluation of the DNA extraction. *Forensic Science International*, 78:103-110.

Grahl, et al. 1996. Killing of microorganisms by pulsed electric fields. *Appl. Microbiol. Biotechnol.*, 45:148-157.

Johns, et al. 1994. Improved methods for the detection of *Bacillus anthracis* spores by the polymerase chain reaction. *Letters in Applied Microbiology*, 18:236-238.

Johnson, et al. 2001. Development of a fully integrated analysis system for ions based on ion-selective optodes and centrifugal microfluidics. *Anal.Chem.*, 73:3940-3946.

Kopp, et al. 1998. Chemical amplication: Continuous-flow PCR on a chip. *Science*, 280:1046-1048.

Lado, et al. 2002. Alternative food-preservation technologies: Efficacy and mechanisms. *Microbes and Infection*, 4:433-440.

Lagally, et al. 2001. Single-molecule DNA amplification and analysis in an integrated microfluidic device. *Analytical Chemistry*, 73: 565-570.

Levi, et al. 2003. Molecular detection of anthrax spores on animal fibres. *Letters in Applied Microbiology*, 36:418-422.

Mafart, et al. 1997. Modelling the heat stress and the recovery of bacterial spores. *International Journal of Food Microbiology*, 37:131-135.

Mainelis, et al. 1999. Collection of airborne microorganisms by electrostatic precipitation. *Aerosol Science and Technology*, 30:127-144.

Mainelis, et al. 2002a. Collection of airborne microorganisms by a new electrostatic precipitator. *Journal of Aerosol Science*, 33:1417-1432.

Mainelis, et al. 2002b. Design and collection efficiency of a new electrostatic precipitator for bioaerosol collection. *Aerosol Science & Technology*, 36(11):1073-1085.

Mainelis, et al. 2002c. Effect of electrical charges and fields on injury and viability of airborne bacteria. *Biotechnology and Bioengineering*, 79(2):229-241.

Northrup, et al. 1998. A miniature analytical instrument for nucleic acids based in micromachined silicon reaction chambers. *Analytical Chemistry*, 70(5):918-922.

Pugmire, et al. 2002. Surface characterization of laser-ablated polymers used for microfluidics. *Analytical Chemistry*, 74(4):871-878.

Schafer, et al. 2003. Rapid detection and determination of the aerodynamic size range of airborne mycobacteria associated with whirlpools. *Applied Occupational and Environmental Hygiene*, 18(1):41-50.

Schneegaβ, et al. 2001. Miniaturized flow-through PCR with different template types in a silicon chip thermocycler. *Lab on a Chip*, 1:42-49.

Shoffner, et al. 1996. Chip PCR. I. Surface passivation of microfabricated silicon-glass chips for PCR. *Nucleic Acids Research*, 24(2):375-379.

Spilimbergo, et al. 2003. Inactivation of bacteria and spores by pulse electric field and high pressure $CO_2$ at low temperature. *Biotechnology and Bioengineering*, 82(1):118-125.

Sung, et al. 2001. Plastic microchip electrophoresis for genetic screening: The analysis of polymerase chain reactions products of fragile X (CGG)n alleles. *Electrophoresis*, 22:1188-1193.

Tsong, T. Y. 1991. Electroporation of cell membranes. *Biophysical Journal*, 60:297-306.

Tsong, et al. 1999. Biological effects of electric shock and heat denaturation and oxidation of molecules, membranes, and cellular functions. *Annals New York Academy of Sciences*, 888:211-232.

Vincent, et al. 1999. Application of recent advances in aerosol sampling science towards the development of improved sampling devices: The way ahead. *J. Environ. Monit.*, 1:285-292.

International Search Report dated Aug. 19, 2005 for PCT/DK2005/000132.

International Preliminary Report on Patentability dated Mar. 20, 2006 for PCT/DK2005/000132.

Co-pending U.S. Appl. No. 10/590,632, filed Aug. 23, 2006, titled Method, Chip, Device and System for Extraction of Biological Materials.

Co-pending U.S. Appl. No. 10/590,648, filed Aug. 23, 2006, titled Method, Kit and System for Enhanced Nested PCR.

Co-pending U.S. Appl. No. 10/590,768, filed Aug. 24, 2006, titled Method, Chip, Device and System for Collection of Biological Particles.

Brown, K. L. 1994. Spore resistance and ultra heat treatment processes. *Journal of Applied Bacteriology Symposium Supplement*, 76:67S-80S.

Lee, et al. 1987. Electrical injury mechanisms: Electrical breakdown of cell membranes. *Plastic and Reconstructive Surgery*, 80(5):672-679.

Riley, R. L. 1974. Airborne infection. *The American Journal of Medicine*, 57:466-475.

Huang, Ying et al.; MEMS-Based Sample Preparation for Molecular Diagnostics; Anal Bioanal Chem; 2002; pp. 49-65, vol. 372; Springer-Verlag.

O'Brien, Dennis et al.; Size and Concentration Measurement on an Industrial Aerosol; Am. Ind. Hyg. Assoc. J; Jul. 1986; pp. 386-392, vol. 47(7); American Industrial Hygiene Association.

Lee, Sang-Wook et al.; A Micro Cell Lysis Device; Sensors and Actuators; 1999; pp. 74-79, vol. 73; Elsevier Science S.A.

Cheng, Jing et al.; Isolation of Cultured Cervical Carcinoma Cells Mixed with Peripheral Blood Cells on a Bioelectronic Chip; Anal. Chem; 1998; pp. 2321-2326, vol. 70; American Chemical Society.

Mainelis, G et al.; Application of Electrostatic Precipitation for Simultaneous Determination of Culturable and Total Airborne Microorganism; Abstracts of the General Meeting of the American Society for Microbiology; 2003; pp. 1-4, vol. 103.

Pappaert, K et al.; Diffusion-Reaction Modelling of DNA Hybridization Kinetics on Biochips; Chemical Engineering Science; 2003; pp. 4921-4930, vol. 58; Elsevier Ltd.

International Search Report dated Aug. 19, 2005 for PCT/DK2005/000130.

International Preliminary Report on Patentability dated Mar. 20, 2006 for PCT/DK2005/000130.

International Search Report dated Aug. 17, 2005 for PCT/DK2005/000133.

International Preliminary Report on Patentability dated Feb. 6, 2006 for PCT/DK2005/000133.

* cited by examiner

METHOD, CHIP, DEVICE AND SYSTEM FOR EXTRACTION OF BIOLOGICAL MATERIALS

CROSS REFERENCE TO RELATED APPLICATION

This application is a U.S. National Phase of PCT International Application Number PCT/DK2005/000132, filed on Feb. 25, 2005, designating the United States of America and published in the English language, which claims priority under 35 U.S.C. §119 to Denmark Application Number PA 2004 00305 filed on Feb. 26, 2004. The disclosures of the above-described applications are hereby incorporated by reference in their entirety.

FIELD OF THE INVENTION

The present invention relates to a method, a chip, a device and a system for extraction of biological material form biological cells. The invention involves exposing the biological particles to an alternating electric field in a sample chamber and may also involve subsequent analysis of the biological material after the extraction.

BACKGROUND

In response to Bioterrorism threats it has become increasingly important to perform rapid and precise detection of biological warfare agents. The *Bacillus anthracis* bacterium is a member of the endospore forming *Bacillus cereus* group. *Bacillus anthracis* is a highly lethal biological warfare agent that is easy to obtain, store, and apply as a bioweapon. In order to make a reliable detection of *Bacillus anthracis* the DNA must be analyzed, since phenotypic differences between the members of the *Bacillus cereus* group in some instances are is less than 1%.

As an example, *Bacillus cereus* differs only from *Bacillus anthracis* because the latter contains two additional plasmids called pXO1 and pXO2. Avirulent strains of *Bacillus anthracis* lacking pXO1 and pXO2 are virtually indistinguishable from *Bacillus cereus*. Theoretically, transfer of the pXO1 and pXO2 plasmids into members of the *Bacillus cereus* group will turn these bacteria into functional *Bacillus anthracis*. For this reason DNA analysis and discrimination of the plasmids pXO1 and pXO2 by means of DNA hybridization, sequencing, or PCR is the only valid method for determining if the detected organism is *Bacillus anthracis*.

Due to their capability to resist harsh environments, the liberation and extraction of DNA from an endospore is a difficult task. The normal procedure used in the detection of *Bacillus anthracis* is to germinate the spores in a culture substrate, collect the bacteria and subsequently extract the DNA from the vegetative bacteria, a procedure that can take many hours up to a day (Levi et al 2003). Other methods include elaborate techniques like mechanical disruption, freeze/thaw cycles or chemical treatment (Johns et al 1994). However, the spore coat and cortex are biochemical structures developed for long term hibernation that can last thousands of years. A famous example is a bacterium revived from an endospore found in the gut of a bee embedded in amber (Cano & Borucki 1995). Furthermore, mechanical disruption (bead beating) results in poor quality of the released DNA (Levi et al 2003). Using present technology, it is possible to release DNA within 5-10 minutes from endospores by combing physical, mechanical, and chemical treatment, but even 5 minutes for DNA extraction is considered long time when the application is a monitoring of bioterrorism attacks carried by aerosols. The use of elaborate multistep procedures is not optimal in the stressful situation that a possible anthrax attack is. For this reason there is a need for a technology that allows rapid (within seconds) hands-off single step DNA extraction from endospores of Gram positive bacteria.

Gram positive bacteria of the genus *Bacillus* and *Clostridia* are capable of undergoing a process at the end of the exponential growth phase called sporulation. During sporulation the bacteria form a rugged spore capable of persisting harsh environments. The spore is a dormant structure with only a few metabolic active enzymes that induced germination when the spore is exposed to nutrients. The spore is very different in its biochemical composition as depicted in Table 1.

TABLE 1

Differences in biochemical composition existing between spores and vegetative cells of *Bacillus* species.

| | Levels of molecules ($\mu$mol/g [dry weight]) | |
|---|---|---|
| Small molecule | *Bacillus* spore | *Bacillus* vegetative cell |
| NADH | <0.002 | 1.95 |
| NAD | 0.11 | 0.35 |
| NADPH | <0.001 | 0.52 |
| NADP | <0.018 | 0.44 |
| ATP | <0.005 | 3.6 |
| ADP | 0.2 | 1 |
| AMP | 1.2-1.3 | 1 |
| 3PGA | 5-18 | <0.2 |
| DPA | 410-470 | <0.1 |
| $Ca^{2+}$ | 380-916 | |
| $Mg^{2+}$ | 86-120 | |
| $Mn^{2+}$ | 27-56 | |
| $H^+$ | 6.3-6.5 | 7.5-8.2 |

The biochemical structures and the dormant physiological state makes the endospore an extremely mechanical, chemical, and heat resistant entity that poses a particular problem in terms of rapid sample preparation and DNA extraction of biological warfare agents for rapid identification. The spores can resist e.g. prolonged boiling without breaking apart. The environmental fate of the spore is not known in detail. The spores can survive 'indefinitely' in dry and protected environments. Excavations in Kruger National Park in South Africa revealed *B. anthracis* spores more than 200 years old (as dated by the $^{14}C$ method) that were still able to germinate in the laboratory.

The most sensitive methods of detecting bacteria and vira rely on gaining access to the intracellular components of the organisms, such as their genetic material.

US 2003/0,146,100 discloses dielectrophoretic separation of cells from blood followed by electronic lysis on isolated cells and digestion, performed on one chip with an electrode array in a flow chamber. Electrophoresis performed with 10 KHz sinusodial field and lysis performed with a series of 400 pulses of 500V and 50 $\mu$s duration or 40 pulses of 200V and 10 $\mu$s duration (square wave).

US 2002/0115201 discloses cell lysis using microwaves in the range of 2.45-310 GHz thereby releasing DNA from cells in liquid suspension. It furthermore discloses a chamber with parallel planar external electrodes for applying microwaves, the chamber have flow channels for providing sample in chamber.

U.S. Pat. No. 4,970,154 discloses a method for inserting foreign genes into cells using pulsed radiofrequency. It furthermore describes electroporation and fusion of cells suspended in a solution in a chamber using pulsed radiofrequency oscillating electrical fields between electrodes in the chamber. Frequency varies from 60 Hz to 10 MHz, fields strength of 100-400 V/cm.

SUMMARY OF THE INVENTION

An object of the present invention relates to the provision of methods, chips, devices and systems for extraction, i.e. gaining access to biological material of biological cells.

Another object of the present invention relates to the provision of methods, chips, devices and systems for extracting biological material of biological cells at high release percentage, i.e. the biological material is extracted or release from a large percentage of the biological cells.

Another object of the present invention relates to the provision of methods, chips, devices and systems for extracting biological material from biological cells without damaging the biological material.

Still another object of the present invention relates to the provision of methods, chips, devices and systems that easily allows for further analysis of extracted biological material.

Yet another object of the present invention relates to the provision of methods, chips, devices and systems in which extraction of biological material and subsequent analysis of the biological material are performed in the same structure and preferably in the same chamber.

Other objects of the invention will become apparent when reading the description and the examples.

An aspect of the present invention relates to a method for extracting biological material from a biological cell, the method comprising the steps of:
  a) providing a sample chamber and a first and a second electrode, the first and the second electrode and the sample chamber being so positioned that at least a part of the sample chamber is between the first and the second electrode,
  b) providing a liquid sample in the sample chamber, which liquid sample comprises a biological cell,
  c) exposing said liquid sample to an alternating electric field in said sample chamber, said alternating electric field being provided by the first and the second electrode and having a sufficient amplitude so as to extract biological material from the biological cell.

In a preferred embodiment of the invention, the method furthermore comprises a step (d) of performing an analysis on a part of the exposed liquid sample, said part comprising extracted biological material from the biological cell. The analysis may e.g. comprise a genetic analysis or a protein analysis.

Another aspect of the invention relates to a chip for extracting biological material from a biological cell, the chip comprising a sample chamber comprising:
  a sample chamber comprising a first opening in fluid connection with the surrounding air and a second opening to form a fluid connection with a device, and
  a first and a second electrode positioned at opposing sides of the sample chamber.

Another aspect of the invention relates to a device for extracting biological material from a biological cell, the device comprising:
  a chip site where the chip is to be located in order be functionally associated with the device,
  an electrical interface between the device and the chip for applying an alternating electric field between the electrodes of the sample chamber, and
  a programmable unit comprising a software that effects that the device performs one or more actions selected from the group consisting of:
    checking if the chip is functionally associated with the device,
    providing a liquid sample in sample chamber, which liquid sample comprises a biological cell,
    exposing said liquid sample to an alternating electric field in said sample chamber, said alternating electric field being provided by the first and the second electrode and having a sufficient amplitude so as to extract biological material from the biological cell, and
    performing a analysis on a part of the exposed liquid sample which part comprises extracted biological material from the biological cell.

Yet an aspect of the invention relates to a system for extracting biological material from a biological cell, the system comprising a chip as defined herein functionally associated with a device as defined herein.

BRIEF DESCRIPTION OF THE FIGURES

In the following some embodiments of the present invention will be described with reference to the figures, wherein.

DETAILED DESCRIPTION OF THE INVENTION

Figure 1:
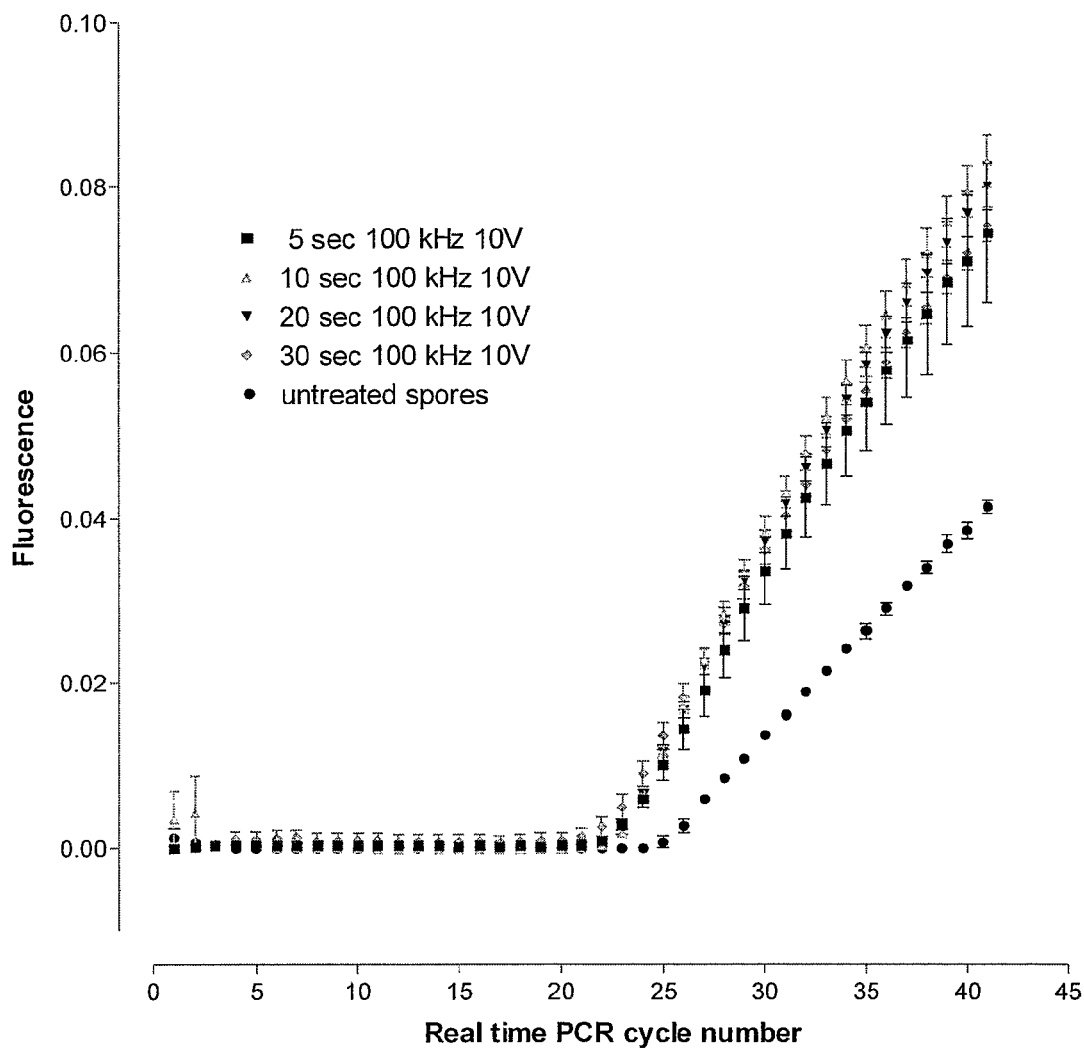
FIG. 1 shows the effect of the duration of exposure to the alternating electric field on the DNA/RNA release percentage (measured via real-time PCR and fluorescence)

An aspect of the present invention relates to a method for extracting biological material from a biological cell, the method comprising the steps of:
  a) providing a sample chamber and a first and a second electrode, the first and the second electrode and the sample chamber being so positioned that at least a part of the sample chamber is between the first and the second electrode,
  b) providing a liquid sample in the sample chamber, which liquid sample comprises a biological cell,
  c) exposing said liquid sample to an alternating electric field in said sample chamber, said alternating electric field being provided by the first and the second electrode and having a sufficient amplitude so as to extract biological material from the biological cell.

In a preferred embodiment of the invention, the method furthermore comprises a step (d) of performing an analysis on a part of the exposed liquid sample, said part comprising extracted biological material from the biological cell. The analysis may e.g. comprise a genetic analysis or a protein analysis.

The genetic analysis may e.g. comprise processes such as incubation with restriction enzymes, nucleic acid amplification such as the PCR process, electrophoresis, and detection such as e.g. fluorescence detection or electrochemical detection. The PCR process and the detection may e.g. be performed according to the methods and using the kits described in the co-pending PCT application "Method, kit and system for enhanced nested PCR" having the Application No. PCT/DK2005/000131 (WO2005/083114 A1), which is incorporated herein by reference.

In a preferred embodiment of the invention, the part of the exposed liquid sample, on which further genetic analysis is performed, comprises at least 20% of the liquid sample in the sample chamber, such as at least 30, 40, 50, 60, 70, 80, 90, 95, 97.5, 99, 99.5, or 99.9% of the liquid sample in the sample chamber, such as at least approximately 100% of the liquid sample in the sample chamber.

According to the present invention, the terms "extraction" and "extracting" relate to releasing biological material of the one or more biological cells, that is to say, e.g. making the biological material available for further analysis in the liquid sample. The terms "extraction" and "extracting" are also related to e.g. opening and/or rupturing the cell wall or cell barrier of the biological cell sufficiently to allow the biological material to escape into the surrounding liquid. After the biological material has been extracted it may still be located near the biological cell or it may be transported to another location, e.g. by electrophoretic forces. The biological material may e.g. be adsorbed onto a electrode after electrophoretic transportation.

In the present context the term "biological cell" is related to a particle comprising e.g., a microorganism, a virus, a eukaryote cell or a fragment thereof.

The eukaryote cell may e.g. be a plant cell, a plant spore, a animal cell such as mammal cell. The mammal cell may e.g. be a human cell, such as a white blood cell or a nucleated red blood cell.

The microorganism may e.g. be selected from the group consisting of an archeal microorganism, a eubacterial microorganism or a eukaryotic microorganism.

E.g., the microorganism may be selected from the group consisting of a bacterium, a bacterial spore, a virus, a fungus, and a fungal spore.

In a preferred embodiment of the invention, the biological cell is an airborne microorganism.

In a preferred embodiment of the invention, the biological cell is a bacterial spore.

For example, the bacterial spore may be formed by a bacterium selected from the genus *Bacillus* and/or the genus *Clostridium*.

In a preferred embodiment of the invention, the bacterial spore is a spore formed by *Bacillus anthracis*. The biological cell may e.g. comprise a bacterial spore formed by *Bacillus anthracis*. Also, the biological cell may essentially consist of one or more bacterial spores formed by *Bacillus anthracis*.

Also, the biological cell may be a vegetative bacterium, or a spore.

The biological material extracted from the biological cell typically comprises a component selected from the group consisting of a cell organelle, a genetic material, and a protein.

The genetic material may e.g. comprise chromosomal DNA and/or plasmid DNA and/or any type of RNA.

The protein may e.g. be selected from the group consisting of enzymes, structural proteins, transport proteins, ion channels, toxins, hormones, and receptors.

Preferably, the biological material comprises DNA and/or RNA.

According to the present invention the term "liquid sample" relates to a liquid substance, a solution or suspension, which may or may not comprise one or more compounds of interest. The liquid sample may e.g. be a biological sample or a non-biological sample.

A biological sample may e.g. be selected from the group consisting of dermal swabs, cerebrospinal fluid, blood, sputum, bronchio-alveolar lavage, bronchial aspirates, lung tissue, and urine.

Non-biological samples may for example be a liquid suspension comprising powders, particles from air samples, and particles from earth samples and surface swipes.

Biological or non-biological samples can be cultured. The culture then can be evaluated for the presence of e.g. a microorganism, such as *B. anthracis*, using the methods, kits, chips, devices and systems of the invention.

Additionally the liquid sample may comprise one or more reagents required to perform a nucleic acid amplification.

The liquid sample may comprise one or more reagents selected from the group consisting of a primer, a nucleic acid, a deoxynucleotide triphosphate and a nucleic acid polymerase.

The liquid sample may furthermore comprise additives such as 2-mercaptoethanol, e.g. in a concentration of 10 mM, BSA in a concentration of e.g. 1 mg/ml and/or a detergent in a concentration of e.g. 0.5% to 6% (w/v). The detergent may be selected from the group consisting of Triton X-100, Triton X-114, NP-40, Tween20, Tween80 and similar non-ionic detergents.

In the present context, the term "nucleic acid", "nucleic acid sequence" or "nucleic acid molecule" should be interpreted broadly and may for example be an oligomer or polymer of ribonucleic acid (RNA) or deoxyribonucleic acid (DNA) or mimetics thereof. This term includes molecules composed of naturally-occurring nucleobases, sugars and covalent internucleoside (backbone) linkages as well as molecules having non-naturally occurring nucleobases, sugars and covalent internucleoside (backbone) linkages which function similarly or combinations thereof. Such modified or substituted nucleic acids may be preferred over native forms because of desirable properties such as, for example, enhanced affinity for nucleic acid target molecule and increased stability in the presence of nucleases and other enzymes, and are in the present context described by the terms "nucleic acid analogues" or "nucleic acid mimics". Preferred examples of nucleic acid mimetics are peptide nucleic acid (PNA-), Locked Nucleic Acid (LNA-), xylo-LNA-, phosphorothioate-, 2'-methoxy-, 2'-methoxyethoxy-, morpholino- and phosphoramidate-comprising molecules or functionally similar nucleic acid derivatives.

The term "nucleic acid polymerase" relates to a DNA- or RNA-dependent DNA polymerase enzyme that preferably is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from thermophilic or caldoactive strains such as *Thermus flavus, T. ruber, T. thermophilus, T. aquaticus, T. lacteus, T. rubens, Thermococcus litoralis, Pyrococcus furiosus, Bacillus stearothermophilus* and *Methanothermus fervidus*. Nonetheless, polymerases that are not thermostable also can be employed in nucleic acid amplification provided the enzyme is replenished.

The liquid sample may furthermore comprise a 5'-3' exonuclease degradable, oligo-nucleic acid probe, the degradation of said nucleic acid probe resulting in release of a redox active component.

The redox active component may e.g. be a metallocene such as e.g. ferrocene.

In an embodiment of the invention, the first and a second electrode are separated by a distance being at the most 20 mm, preferably being at the most 20 mm, such as at most 15 mm, 10 mm, 9 mm, 8 mm, 7 mm, 6 mm, 5 mm, or at most 4 mm, more preferably being at the most 3 mm, and even more preferably at most 0.5 mm such as at most 0.3 mm, 0.2 mm, 0.1 mm, such as at most 0.05 mm.

For example the first and the second electrode may be separated by a distance in the range of 0.05-20 mm, such as in the range of 0.05-0.1, 0.1-0.2, 0.2-0.3, 0.3-0.4, 0.4-0.5, 0.5-1, 1-2, 2-5, 5-10, or 10-15 mm, such as in the range of 15-20 mm.

Typically, the first and the second electrode are be separated by a distance, which is at least 0.02 mm such as at least 0.03 mm or 0.05 mm.

Normally, at least a part of the liquid sample in sample chamber is positioned between the first and the second electrode. For example, at least 40% of the volume of the liquid sample is positioned between the first and the second electrode, such as at least 50, 60, 70, 80, 90, 95, 97.5, 99, 99.5, or 99.9% of the volume of the liquid sample is positioned between the first and the second electrode, such as at least 100% of the volume of the liquid sample is positioned between the first and the second electrode.

Preferably the biological cell is located between the first and the second electrode during step (c). The biological cell may even be attached to the first or the second electrode at least initially in step (c) and possibly also during step (c).

The term "and/or" used in the context "X and/or Y" should be interpreted as "X", or "Y", or "X and Y".

The chip of the present invention comprises a sample chamber comprising a first opening.

The first opening may be used for introducing sample in to the sample chamber. The first opening may be in fluid connection with a sample, e.g. the surrounding air. Alternatively, the first opening is connected to one or more valve(s), which valve(s) may be opened to bring the sample chamber in fluid connection with the sample.

In an important embodiment of the invention, the sample chamber, e.g. the sample chamber of the chip, comprises a second opening. The second opening may e.g. be use for facilitating the introduction of new sample into the sample chamber by allowing air or sample of the sample chamber to escape. The second opening may also be used for introducing a first liquid reagent into the sample chamber. Alternatively the first liquid reagent may enter the sample chamber via the first opening.

The sample chamber, e.g. the sample chamber of the chip, is typically a microscale sample chamber. In an embodiment of the invention, the volume of the sample chamber is at most 500 µL such as at most 400 µL, 300 µL, 200 µL, 100 µL, 50 µL, 25 µL, 15 µL, 10 µL, 5 µL, 4 µL, 3 µL, or at most 2 µL, such as at most 1 µL. For example, the volume of the sample chamber may be at most 500 nL such as at most 400 nL, 300 nL, 200 nL, 100 nL, 50 nL, 25 nL, 15 nL, 10 nL, 5 nL, 4 nL, 3 nL, or at most 2 nL, such as at most 1 nL.

Typically, the volume of the sample chamber is at least 10 nL. In a preferred embodiment of the invention, the volume of the sample chamber is in the range of 1 µL-50 µL, such as 5 µL-30 µL.

In an embodiment of the invention, the smallest distance between a pair of opposing walls is at most 20 mm, such as at most 15 mm, 10 mm, 8 mm, 6 mm, 4 mm, 3 mm, or 2 mm, such as at most 1 mm. For example, the smallest distance between a pair of opposing walls is at most 800 µm such as at most 600 µm, 500 µm, 400 µm, 300 µm, 200 µm, 100 µm, 50 µm, 25 µm, 15 µm, 10 µm, 5 µm, 4 µm, 3 µm, or at most 2 µm, such as at most 1 µm.

Typically, the smallest distance between a pair of opposing walls is at least 5 µm. In a preferred embodiment of the invention, the smallest distance between a pair of opposing walls is the range of 50 µm-500 µm, such as 100 µm-400 µm, and 150 µm-350 µm.

In an embodiment of the invention, the length of the sample chamber, e.g. the sample chamber of the chip, is in the range of 1 mm-50 mm, such is in the range of 1 mm-10 mm, 10 mm-20 mm, 20 mm-30 mm, 30 mm-40 mm, or 40 mm-50 mm. In a preferred embodiment the length of the sample chamber is in the range of 2 mm-8 mm, such as 3 mm-7 mm or 4 mm-6 mm. For example, the length of the sample chamber may be about 4.5 mm.

In an embodiment of the invention, the width of the sample chamber, e.g. the sample chamber of the chip, is in the range of 0.2 mm-10 mm, such is in the range of 0.2 mm-1 mm, 1 mm-3 mm, 3 mm-5 mm, 5 mm-7 mm, or 7 mm-10 mm. In a preferred embodiment the width of the sample chamber is in the range of 0.2 mm-2 mm, such as 0.5 mm-1.5 mm and 0.75 mm-1.25 mm. For example, the width of the sample chamber may be about 1 mm.

In an embodiment of the invention, the height of the sample chamber, e.g. the sample chamber of the chip, is in the range of 50 µm-2 mm, such is in the range of 100 µm-1 mm, 200 µm-900 µm, 300 µm-800 µm, 500 µm-700 µm. In a preferred embodiment the height of the sample chamber is in the range of 100 µm-400 µm, such as 200 µm-300 µm.

In an embodiment of the invention, the length of the sample chamber, e.g. the sample chamber of the chip is approximately 4.5 mm, the width of the sample chamber is approximately 1 mm and the height of the sample chamber is approximately 300 µm.

In an embodiment of the present invention the chip furthermore comprises a first and a second electrode.

The first and/or the second electrode may have different shapes or dimensions. For example, the first and/or the second electrode may have a substantial form chosen from the group of a sheet, a plate, a disc, a wire, a rod; or any combination thereof.

In a preferred embodiment of the present invention, the first and the second electrode may e.g. be sheet-like electrodes.

In a preferred embodiment of the present invention the first electrode and the second electrode are facing each other. For example, they may be positioned at opposite sides of the sample chamber.

The first electrode and/or the second electrode may e.g. be positioned inside the sample chamber, standing free in the sample chamber or attached to one or more of the wall of the sample chamber.

The first and/or the second electrode(s) may be embedded in the sample chamber wall(s). For example, the first and the second electrode(s) may be embedded in the sample chamber walls. Alternatively, the first and/or the second electrode(s) may be positioned in the outer surface(s) of the chip.

Preferably the first electrode and the second electrode are positioned at opposite sides of the sample chamber.

The potential difference between the first and second electrode may be in a range that causes particles of uniform or dissimilar sizes to be captured onto a surface or deflected in a given direction that can accommodate a selection or capture of the particles of interest.

An electrode, e.g. the first electrode and/or the second electrode may be formed in a number of different materials. Typically, the electrodes are formed in metals or alloys. The first and the second electrode may for example comprise a metal selected from the group consisting of silver, gold, platinum, copper, carbon, iron, graphite, chrome, nickel, cobalt, titanium, mercury or an alloy thereof.

It is also envisioned that an electrode may comprise a conducting liquid and even essentially consist of a conducting liquid. The conducting liquid may e.g. be mercury.

The dimension or/and structure of electrodes typically depend on the dimension and/or structure the sample chamber. The length and width of the electrodes are of the same order of magnitude as the length and width of the sample chamber.

The electrodes can be formed by as little as a coating of a few atom layers of conductive material.

In an embodiment of the invention, an electrode, e.g. the first and/or the second electrode, has a thickness in the range of 0.001 µm-2000 µm, such as 0.001 µm-1 µm, 1 µm-20 µm, 20 µm-200 µm, and 200 µm-2000 µm.

In an embodiment of the invention, the sample chamber of the chip furthermore comprises a set of detection electrodes, e.g. two or three detection electrodes, for the detection of the presence or absence of redox active component, which e.g. may be released from a probe. Two detection electrodes may serve as working electrode and counter electrode, respectively. The set of detection electrodes may furthermore comprise a reference electrode. Typically, the detection electrodes are formed in metals or alloys. The electrodes may for example comprise a material selected from the group consisting of carbon, silver, gold, or platinum. After detection, the electrodes may suffer from film formation on the electrode surface. To permit further detection of digested probe, further sets of detection electrodes can be placed within the sample chamber of the chip.

In an embodiment of the invention, the first and second electrode may be the set of detection electrodes.

In a preferred embodiment of this invention, the chip furthermore comprises a temperature-sensing element, which e.g. could be a thermally sensitive metal-based resistor (a thermistor) with a positive temperature coefficient (PTC) i.e., the thermistor exhibits increasing electrical resistance with increases in environmental temperature and decreasing electrical resistance with decreasing temperature.

The thermistor may e.g. be selected from the group of materials comprising copper, nickel, iron, aluminium, platinum, or alloys hereof.

The thermistor may have different shapes or dimensions. For example, the thermistor may have a substantial form chosen from the group of a sheet, a plate, a disc, a wire, or a rod.

The thermistor may e.g. be a wire-formed electrode.

The heating electrode may have different shapes or dimensions. For example, the heating electrode may have a substantial form chosen from the group of a sheet, a plate, a disc, a wire, or a rod.

In a preferred embodiment of the present invention, the heating electrode may e.g. be a sheet-like electrode. In a preferred embodiment of the present invention the heating electrode may be positioned to enable heating from at least one side of the reaction chamber.

In yet another embodiment, one or more supplementary heating electrodes may be positioned on the opposing sides of the reaction chamber.

The heating electrode is made of electrically conductive material, preferably selected from the group of nickel-chrome (NiCr), iron-chrome-aluminum (FeCrAl), iron-nickel-chrome (FeNiCr) or other heating element alloys.

In a preferred embodiment of the invention, the chip comprises one or more conducting contact pads in electrical contact with the electrodes of the chip. The chip may comprise a conducting contact pad in electrical contact with the first electrode. The chip may comprise a conducting contact pad in electrical contact with the second electrode. The chip may comprise two conducting contact pads in electrical contact with each their end of the heating electrode. The chip may comprise two or three conducting contact pads in electrical contact with each their electrode of the set of detection electrodes.

In FIG. 1, two exemplary chip embodiments are illustrated. In FIG. 1 A) the chip (1) comprises the sample chamber (2) and a first electrode (3) and second electrode (4). The first electrode (3) is attached to the upper part (5) of the chip and the second electrode (4) is attached to the lower part (6) of the chip. Both the first and second electrodes are covered by an electrically insulating layer (7) to prevent unwanted electrolysis of the liquid contents of the sample chamber (2). A heating electrode is embedded in the insulating layer on top of the second electrode. The sample chamber is formed via a spacer part (9), which is sandwiched between the first part (5) and the second part (6) of the chip (1). The set of detection electrodes and the temperature sensing element are not shown in FIG. 1.

The chip may comprise a vast array of different materials. It may for example comprise organic polymers such as plastics, metals and semiconductors such as silicon, glasses and ceramics and so fort.

With respect to FIG. 1, the first and second parts could e.g. comprise materials such as plastics, semiconductors such as silicon, glasses or ceramics. The first and second electrode could e.g. comprise a metal such as gold or copper. The insulating layer could e.g. be a film of $SiO_2$ or polyimide. The heating electrode could e.g. be a NiCr electrode and the spacer layer might e.g. be cast a polydimethylsiloxane (PDMS) elastomer.

In FIG. 1 B) the first and second electrode are not comprised by the chip but may e.g. be comprised by a device for operating the chip.

The chip may comprise just a single sample chamber or it may comprise multiple sample chambers.

A chip typically has a thickness in the range of 0.5 mm-50 mm, and preferably in the range of 2 mm-8 mm.

A chip typically has a length or diameter in the range of 10 mm-500 mm, preferably in the range of 40 mm-200 mm.

A chip typically has a width in the range of 5 mm-200 mm, preferably in the range of 20 mm-100 mm.

In step c) the liquid sample is exposed to an alternating electric field, which is provided by the first and the second electrode. It is important that the alternating electric field has a sufficient amplitude and is applied for a sufficient duration of time to extract biological material from the biological cell.

According to the present invention, the term "alternating electric field" relates to electric fields that change over time. The alternating electric field may e.g. be the electric field that occurs from periodically shifting the polarity of two electrodes between positive/negative and negative/positive, e.g. by connecting an AC source to the electrodes. The alternating electric field may e.g. comprise or be an AC field. The alternating electric field may e.g. comprise one or more DC pulses.

It is important that the alternating electric field has a sufficient amplitude and is applied for a sufficient duration of time to extract the biological material. It may also be important that the alternating electric field furthermore has a sufficient frequency to extract the biological material.

In a preferred embodiment of the invention, the frequency of the alternating electric field is at the least 5 kHz, preferably being at least 20 kHz, and more preferably being at least 50 kHz.

In another preferred embodiment of the invention, the frequency of the alternating electric field is at the least 100 kHz, preferably being at least 250 kHz, and more preferably being at least 500 kHz.

For example, the frequency of the alternating electric field may be at least 5 kHz, such as at least 10, 20, 50, 100, 200, 300, or 400 kHz, such as at least 500 kHz. Even higher frequencies such as 1000 kHz, 2000 kHs or 5000 kHz is envisioned.

Preferably the frequency of the alternating electric field is at most 750 kHz, such as at most 500 kHz.

Thus, the frequency of the alternating electric field may e.g. be in the range of 5-750 kHz, such as in the range of 5-10, 10-20, 20-50, 50-100, 100-200, 200-300, 300-400, 400-500 kHz, such as in the range of 500-750 kHz.

In a preferred embodiment, the alternating electric field provided by modulating the polarity of the two electrodes.

The alternating electric field may have a substantial form chosen from the group consisting of: rectangular, sinusoidal, saw-tooth, asymmetrical triangular, symmetric triangular; or any combination thereof.

Also, the alternating electric field, in the frequency domain, may comprise a least a first and a second frequency component.

The amplitude of the alternating electric field, that is, the maximum potential difference between the first and the second electrode, is typically at most 30 V, such as at most 25, 20, 15, 10, 8, 6, 5, 4, 3, or 2 V, such as at most 1 V.

The amplitude of the alternating electric field, that is, the maximum potential difference between the first and the second electrode, may e.g. be in the range of 1-100 V, such as in the range of 1-2, 2-3, 3-4, 4-5, 5-6, 6-8, 8-10, 10-15, 15-20, or 20-30 V, such as in the range of 30-100 V. Preferably, the maximum potential difference between the first and the second electrode is in the range of 5-50 V such as 10-25 V.

A useful measure of yield of the extraction of biological material is the DNA/RNA release percentage. The "DNA/RNA release percentage" is percentage of biological cells in the sample chamber that release their chromosomal DNA and/or chromosomal RNA due to the exposure in step c) to the alternating electric field. The DNA/RNA release percentage is determined according to the standardised method described in Example 5.

The extraction and thus the DNA/RNA release percentage of biological cells in the sample chamber or in a chip comprising the sample chamber is strongly dependent on the design of and the distance between the first and the second electrode, the structure and materials of the sample chamber and the potentials applied to the first and the second electrode.

In a highly preferred embodiment of the invention, the first potential of the first electrode and the second potential of the second electrode, and thus the alternating electric field between the first and the second electrode, are modulated so as to yield a DNA/RNA release percentage of at least 30%, such as a DNA/RNA release percentage of at least 40%, preferably of at least 50%, and more preferably of at least 60%, such as of at least 70%, 80%, 90%, 95%, 97.5%, 99%, 99.5% or 99.9% such as approximately of 100%.

In an another preferred embodiment of the invention, the first potential of the first electrode and the second potential of the second electrode, and thus the alternating electric field between the first and the second electrode, are modulated so as to yield a DNA/RNA release percentage of at least 30% of the bacterial spores in the sample chamber, such as a DNA/RNA release percentage of at least 40%, preferably of at least 50%, and more preferably of at least 60% of the bacterial spores in the sample chamber, such as of at least 70%, 80%, 90%, 95%, 97.5%, 99%, 99.5% or 99.9% such as approximately of 100% of bacterial spores in the sample chamber.

In an embodiment of the invention, the duration of which the liquid sample is exposed to the alternating electric field is at most 3600 seconds, such as at most 3000, 2000, 1000, 500, 250, 100, 50, 40, 30, 20, 10, 5, 4, or 3 seconds, such as at most 1 seconds.

For example, the duration of which the liquid sample is exposed to the alternating electric field is in the range of 0.01-3600 seconds, such as in the range of 0.1-1, 1-5, 5-10, 10-25, 25-50, 50-100, 100-250, 250-500, 500-1000, or 1000-2000 seconds, such as in the range of 2000-3600 seconds. In a preferred embodiment of the invention, the duration of which the liquid sample is exposed to the alternating electric field is in the range of 5-100 seconds, such as 6-90 seconds, 7-80 seconds, 8-70 seconds, 9-60 seconds and 10-50 seconds.

In a preferred embodiment of the invention, the liquid sample is exposed to the alternating electric field for at most 250 second, preferably for at most 100 second such as for at most 30 seconds.

Another aspect of the invention relates to a chip for extracting biological material from a biological cell, the chip comprising a sample chamber comprising:
  a sample chamber comprising a first opening in fluid connection with the surrounding air and a second opening to form a fluid connection with a device, and
  a first and a second electrode positioned at opposing sides of the sample chamber.

In a preferred embodiment of the invention, the sample chamber of the chip furthermore comprises a liquid sample comprising a biological cell.

The chip may furthermore comprise an alternating electric field between and provided by first and the second electrode, said alternating electric field having a sufficient amplitude so as to extract biological material from the biological cell.

In an embodiment of the invention, the first and a second electrode of the chip are positioned between the first and the second opening of the sample chamber.

The biological cell is preferably located between the first and the second electrode of the chip.

It should be noted that embodiments and features described in the context of one aspect of the present invention also are applicable for the other aspects of the invention.

Another aspect of the invention relates to a device for extracting biological material from a biological cell, the device comprising:
  a chip site where the chip is to be located in order be functionally associated with the device,
  an electrical interface between the device and the chip for applying an alternating electric field between the electrodes of the sample chamber, and
  a programmable unit comprising a software that effects that the device performs one or more actions selected from the group consisting of:

checking if the chip is functionally associated with the device, providing a liquid sample in sample chamber, which liquid sample comprises a biological cell, exposing said liquid sample to an alternating electric field in said sample chamber, said alternating electric field being provided by the first and the second electrode and having a sufficient amplitude so as to extract biological material from the biological cell, and performing a analysis on a part of the exposed liquid sample which part comprises extracted biological material from the biological cell.

In the present context the term "functionally associated" means that the chip is associated with the device, so that the device can perform one or more actions affecting the chip.

In an embodiment of the invention, the chip is functionally associated with the device when the device can affect the electric field of the contents of the sample chamber.

In an embodiment of the invention, the chip is functionally associated with the device when the device can control the potential of at least one electrode of the chip. For example, the device may be functionally associated with the chip when the device can control the potential of the first electrode and/or the second electrode of the chip.

Being functionally associated may furthermore include that the sample chamber of the chip is in fluid communication with a flow controlling means.

In an embodiment of the invention, the device comprises a set of collection electrodes, and when the chip is functionally associated an electrical field between the set of collection electrodes assist collecting the biological cells of the gaseous sample in the sample chamber. In this embodiment, the chip need not comprise the set of collection electrodes.

The device may also comprise a first reagent chamber for receiving and/or holding a first liquid reagent. Typically, the first reagent chamber has at least one opening, which are in fluid connection with the sample chamber when the chip is functionally associated with the device. Alternatively, the at least one opening of the first reagent chamber is brought in fluid connection with the sample chamber e.g. by using the means for controlling a flow. The first reagent chamber may also be closed by a removable barrier during storage, said barrier being removed either reversibly or irreversibly when the device is used.

The device may furthermore comprise an electrical power supply for supplying power, e.g. to the flow generating means, and/or to the programmable unit, the first and second electrodes.

In an embodiment of the present invention, the chip is functionally associated to the device via the chip site. The chip site may e.g. comprise a plastic interface serving both as connecting material and as gaskets ensuring tight junctions between chip-ports and device-ports eliminate leakage of air and liquid. The chip site may for example comprise a surface and/or cradle for receiving the chip. Typically the chip site comprises at least one conducting contact pad. Preferably, the chip site comprises at least a conducting contact pad for providing electrical contact with the first electrode of the chip and a conducting contact pad for providing electrical contact with the second electrode of the chip.

The programmable unit contains instructions, preferably computer readable e.g. software, adapted to facilitate controlling, monitoring, and/or manipulating of the device prior to operation, under operation, and/or after operation.

The programmable unit preferably comprises at least one computer having one or more computer programs stored within data storage means associated therewith, the computer system being adapted to for controlling the device. The programmable unit may in the context of the present invention be chosen from the non-exhaustive group of: a general purpose computer, a personal computer (PC), a programmable logic control (PLC) unit, a soft programmable logic control (soft-PLC) unit, a hard programmable logic control (hard-PLC) unit, an industrial personal computer, or a dedicated microprocessor.

The present invention also relates to a computer program product being adapted to enable a computer system comprising at least one computer having data storage means associated therewith to control, monitor, and/or manipulate the device prior to operation, under operation, and/or after operation. The present invention further relates to a computer readable medium having stored therein a set of routines for enabling a computer system comprising at least one computer having data storage means associated therewith to control, monitor, and/or manipulate the device prior to operation, under operation, and/or after operation.

The programmable unit for controlling, monitoring, and/or manipulating the device prior to operation, under operation, and/or after operation preferably is preferably adapted for operation under harsh conditions, such as artic climate, tropical climate, and combat environment, in particular combat zones having being subjected to atomic, biological, and/or chemical warfare (ABC-warfare). Preferably, the programmable unit complies with the relevant military specifications for such units.

In an embodiment of the invention, the programmable unit comprising the software furthermore effects that the device checks if the chip is functionally associated with the device.

The programmable unit comprising the software may furthermore effect that the device performs one or more actions, such as e.g. 2, or 3 actions, selected from the group consisting of providing a liquid sample in sample chamber, exposing the liquid sample to an alternating electric field in said sample chamber, said alternating electric field and having a sufficient amplitude so as to extract biological material from a biological cell, performing an analysis on the biological material of the exposed liquid sample.

The programmable unit comprising the software may e.g. effect that the device provides a gaseous sample in sample chamber by operating a flow generating means for providing a gaseous sample.

The programmable unit comprising the software may e.g. effect that the device applies a first potential to the first electrode and a second potential to the second electrode.

The programmable unit comprising the software may e.g. effect that the device exposes the reaction mixture to an alternating electric field in said sample chamber by modulating the potentials of at least two electrodes, e.g. the first and the second electrode as described herein or another set of electrodes dedicated to the alternating electric field.

The programmable unit comprising the software may e.g. effect that the device performs a nucleic acid amplification of a target nucleic acid sequence by operating a heating electrode as described herein.

The programmable unit comprising the software may e.g. effect that the device measures the presence of the amplified target nucleic acid sequence and/or measuring products resulting from amplification of the target nucleic acid sequence by operating the detection electrodes related to differential pulse voltammetry.

In a preferred embodiment of the invention, the device furthermore comprises an electrical interface between the device and the chip for applying an electrostatic field between the first and the electrodes of the sample chamber.

The device may additionally measure a reference signal, i.e. a signal from a sample that either comprising a sample without a biological cell or comprises a well defined amount of a given biological cell. The reference signal may e.g. be retrieved from another chamber remote to the sampling chamber, e.g. a chamber located at another position of the chip, or a chamber located at another chip.

The device may furthermore comprise an internal power supply.

The internal power supply may e.g. comprise a battery. The amount of energy to be utilized during a PCR reaction can be estimated as the amount of heat required to heat a volume of water equivalent to that of the fluid sample between the minimum and maximum temperatures of the PCR cycle. This temperature difference is approximately 50 K, and thus the heat to be transferred per cycle is approximately 6 Joules for a 30 µL sample volume. Running for example 60 cycles, the total energy consumption for one PCR reaction amounts to 60*6=360 Joules. Using a ramping time comparable to commercial thermocyclers (i.e. 2° C. per second) the power required is 360*2/50=14.4 W.

The battery voltage is considered to be the rated voltage of the battery, e.g. 1.2V per cell for nickel-cadmium (NiCd) and nickel-metal hydride (NiMH) batteries and 3.6V per cell for most lithium-ion (Li-ion) batteries. The charge capacity of the battery is typically given in terms of milliAmp-hours (mAh) and is called C-rating. For example, a load current of 1C for a battery with a C-rating of 1200 mA-hours is 1200 mA. A battery can be viewed as being ideal, (i.e., with a constant energy capacity) when draining with a load current below 0.1C (Linden, D. 1984. Handbook of Batteries and Fuel Cells. New York: McGraw-Hill). Therefore, when delivering a power output of 14.4 W using e.g. a battery delivering 10.8V, the C-rating of this battery should be in the range of 14.4/(10.8*0.1)=13300 mAh to avoid peak power consumption that will dramatically reduce the energy capacity.

To enable this energy consumption and power delivery, and to further ensure true portability, rechargeable batteries are preferred. In a preferred embodiment of the present invention rechargeable batteries are selected from the group consisting of Nickel Metalhydride (NiMH) based batteries and Lithium-ion (Li-ion) based batteries.

Also, the internal power supply may comprise a generator, e.g. a portable generator. A portable power generator can be utilized as external power supply. The portable power generator can be recharged from, or simply consist of, a solar module, a battery charger (e.g. AC or car battery charger), a fuel combusting generator, or similar.

Alternatively, power from an external power supply can be provided to the device, e.g. supplemented with a battery back-up.

In an embodiment of the invention, the device furthermore comprises a flow generating means e.g. for providing a gaseous sample in the sample chamber of the chip and being in fluid connection with the second opening of the sample chamber when the chip is inserted in the device.

The flow generating may comprise a pump such as a piston pump, a membrane pump, or a positive displacement pump.

In an embodiment of the present invention, the pump is able to deliver an appropriate air-flow through the chip during sampling (in the range of 10 mL/min to 500 mL/min) is selected. Preferably, the pump should be selected to fulfil one or more of the following criteria: small size, lightweight, pulsation-free flow, reversible flow of the medium by changing motor polarity, flow volume adjustable by controlling voltage.

In an embodiment of the invention, the flow generating means may comprise an inkjet dispenser for creating small droplets of reagent or a similar micro dispensing device.

In an embodiment of the present invention, the gaseous sample can be provided by a passive flow through the chip. This will demand a velocity difference between the chip and the surrounding air to be sampled. For example, the chip may be moved through the air, e.g. mounted on an airplane in such a way that the first opening is in fluid connection with the surrounding air, optimally opposing the flight direction. Alternatively, the conditions occur if the air is moving around the chip having no velocity compared to the air, e.g. mounted in an air vent.

In an embodiment of the invention, the device furthermore comprises a means for controlling, e.g. a flow through the sample chamber.

The flow may e.g. be a liquid flow and/or a gas flow.

The means for controlling a flow typically comprises one or more valves. The valves may e.g. be selected from the group consisting of a check valve, a two way valve, a multi position valve and a pinch valve.

The valve may e.g. be a microfabricated valve and in an embodiment the valve is integrated in the chip.

In an embodiment of the present invention, the first reagent liquid can be delivered using the Ink-Jet micro dispensing technology. An Ink-Jet cartridge containing one or more compartments comprising the first liquid reagent or separate components of the first liquid reagent is mounted in such a way that it enables the microdispensing of liquids into the reaction chamber.

In yet another embodiment of the present invention, the first liquid reagent or separate components hereof are encapsulated within sealed envelope being composed of a plastic polymer. The plastic polymer envelope is equipped with a build-in heating electrode, enabling the melting of the plastic polymer by the application of an appropriate electrical current and the subsequent release of the encapsulated liquid into the chip. In yet another embodiment, the release of liquid from the sealed plastic polymer envelope can be achieved by mechanical or physical rupturing of the envelope, e.g. by puncturing the envelope with a sharp object.

In one embodiment of this invention, the device can be equipped with a display enabling a visual readout of the results. The display can be in the format of a light emitting source (a LED, a light bulb or similar), a screen, a digital readout or any combinations of the mentioned. In yet another embodiment of this invention, the readout can be communicated in the form of audio signals.

In a preferred embodiment of this invention, the device comprises a component that allows for wireless communication. Examples of wireless communication are 802.11 Mobile Wireless LAN, cellular, Bluetooth®, GPS, and Ultra Wideband. The communication can be one-way, e.g. transport of data from the device or transport of data to the device, or the communication can be the combination, i.e. two-way. Established communication can further be expanded to inter-device communication, i.e., establishment of an ad-hoc network enabling one device to trigger the initiation of sampling of another device thus facilitating the monitoring of, for example, the progression of an aerosol cloud.

In a preferred embodiment of the invention, the device is a low weight and/or portable device.

In embodiment of the present invention, the device weighs at most 10 kg, such as at most 8 kg, 6 kg, 4 kg, 3 kg, or 2 kg, such as at most 1 kg. It may even be preferred that the device weighs at most 800 g such as at most 600 g, 500 g, 400 g, 300 g, 200 g, 150 g, 100 g, 80 g, 60 g, 50 g, 40 g, 30 g, 20 g, 10 g, or 5 g, such as at most 1 g.

Typically the device has a total weight in the range of 20 g-1 kg, such as 20 g-50 g, 50 g-100 g, 100 g-250 g, 250 g-500 g or 500 g-1000 g.

Yet an aspect of the invention relates to a system for extracting biological material from a biological cell, the system comprising a chip as defined herein functionally associated with a device as defined herein.

In an embodiment of the present invention, the chip and the device of the system are integrated and are not meant to be physically separated from each other. In an embodiment of the invention, the chip and the device of the system are integrated so that they cannot be physically separated from each other without damaging the chip or the device.

In an important embodiment of the present invention, the system is a disposable system, e.g. meant to be used only once.

In another important embodiment the chip of the system is disposable but the device is meant to be reused.

A special aspect of the present invention relates to a method and a microstructure facilitating the method for extracting DNA from endospores of bacteria from the *Bacillus* group.

A purpose of the present invention is to perform a rapid DNA extraction from highly mechanical, chemical, and heat resistant endospores of Gram-positive bacteria, including *Bacillus anthracis*, to enable rapid DNA detection.

This purpose is obtained by a method and a structure comprising the combined usage of a pulsed electrical field induced over the spores, said usage consists of a fluidic structure containing a solution of spores embedded between or adjacent to an electrical field that can be varied in frequency and amplitude and applied for a variable time, and a set of optimal parameter settings for the said usage.

The present invention describes a method that enables the application of a pulsed electrical field across a solution containing spores. As a result of said method DNA is released within a period of 5 seconds after initialization of said method.

In a special embodiment, this invention provides a method for rapid extraction of DNA from spores utilizing a two electrode configuration with an intercalated solution containing endospores. The electrodes are connected to a voltage source and frequency generator allowing a pulsed electrical field to be induced on the solution.

In another special embodiment, the invention utilizes a micro-fluidic device that performs the same functions as above and might be an integrated part of a sample preparation system for rapid DNA extraction.

In yet another special aspect of the invention, the quality of the released DNA as a consequence of the application of said method is not affected as measured by subsequently running PCR or visually inspecting the quality of DNA (after agarose gel electrophoresis and staining).

The issue regarding the amount of the applied potential actually appearing across the solution is particularly important in microstructures using a two electrode configuration for applying an electroporating voltage to the cell or spore solution. Due to this, the voltage drop at the electrode-solution interface is significant in comparison with the applied voltage. To persons skilled in the art, it is well known that the solution used in the experiment sets limits on the potential gradient over time. E.g., a small applied voltage ($<2$ V) results in a very small potential gradient across the electrodes, even at long pulse times ($>100$ μs) generating a peak shaped gradient. The maximum magnitude of applied voltage in solution can be calculated by convoluting the exponential functions for the instrument rise time and charging time. For example, an instrument rise time of 8 μs and a charging time in the range 20-40 μs give a maximum of 15-18% of the applied amplitude. The maximum is achieved approximately 10-15 μs after application of the pulse. After 50-75 μs the potential drop is effectively zero because all the applied voltage appears at the electrode-solution interface. At higher voltages the interfacial impedances becomes negligible and the current that passes between the electrodes is limited by the solution conductance.

The resistance of a 100 mM KCl solution for distances greater than 10 μm is generally found in the range of 30±3 kΩ.

The spore coat consists of protein that gives mechanical protection to the entire spore structure. *Bacillus cereus* has a spore coat that consists of one protein whereas *Bacillus subtilis* has more than 20 proteins have been identified in the coat. Furthermore, the coat is a functional molecular sieve protecting the spore interior against all but the smallest molecules, although the spore coat has be associated with resistance to halogens as chloride and iodine. The coat also participates in germination; it has been shown that spores with mutations in the spore coat also are the most defective in regard of germination.

In the vegetative cell of *Bacillus* species the cell wall peptidoglycan is composed of repeating disaccharides of N-acetylglucosamine (NAG) and N-acetylmuramic acid (NAM) in β-1,4 linkage. Peptide chains (initially L-alanine-D-glutamate-meso-diaminopimelic acid [Dpm]-D-alanine-D-alanine) are attached to the NAM residues; approximately 35% of all PG in vegetative cells participates in cross-linking. In contrast to vegetative cell PG, which can exhibit significant variations between different *Bacillus* species, the basic features of the structure of the cortical PG are similar in all species. The structure of the cortical PG differs in two major respects from that of the vegetative cell PG.

1. Approximately 50% of NAM residues in the cortex are present as muramic acid-rho-lactam (MAL) with the majority of the MAL residues spaced at every second muramic acid position in the glycan strand
2. Approximately 25% of NAM residues carry only a single L-alanine and since MAL residues do not carry a peptide side chain, only ¼ as many Dpm residues are available to participate in cross-link formation in spore cortex compared to the growing cell. As a consequence spore PG is much less cross-linked than in the vegetative cell. However, the exact molecular arrangement in the spore cortex is not known. It has been shown that the spore cortex is involved in osmotic swelling and shrinking of the spore.

As a consequence of the applied and alternating electric potential, chemical alteration of the nucleotide bases of the DNA due to oxidation or reduction reactions at the electrodes could occur. This may possibly result in bad nucleotide recognition by the thermo-stable DNA polymerase during subsequent DNA amplification, yielding reduced amplification rates or misincorporation of nucleotides.

Thus, a special aspect of the present invention relates to a method for making intracellular components accessible from spores by applying a high frequency alternating electrolyzing field.

In a special embodiment of the invention, the method may e.g. be aimed at the extraction of DNA and/or purifying DNA.

In a special embodiment of the invention, the method may also be aimed for use in DNA detection, e.g. in the context of diagnostic analysis.

In a special embodiment of the invention, the method may e.g. be aimed for use in PCR, such as use in integrated PCR devices.

In a special embodiment of the invention, the method may e.g. be aimed for use in mobile PCR devices, or in biological warfare agent detection.

In a special embodiment of the invention, the method may e.g. be aimed at bacterial spores.

In a special embodiment of the invention, the method described herein is aimed at spores from Gram positive bacteria.

In a special embodiment of the invention, the method described herein is aimed at spores from the genus Bacillus and Clostridia.

In a special embodiment of the invention, the method described herein is aimed at spores from the Bacillus cereus group.

In a special embodiment of the invention, the method described herein is aimed at spores from the species Bacillus anthracis.

In a special embodiment of the invention, the method described herein aimed at detecting prokaryotic cells.

In a special embodiment of the invention, the methods described herein, where the aim is to liberate DNA from bacterial cells.

In a special embodiment of the invention, the method herein is aimed at heat resistant bacterial cells.

In a special embodiment of the invention, the method described herein aimed at thermophilic and caldoactive bacteria.

In a special embodiment of the invention, the methods is aimed at the detection of heat resistant bacteria by PCR.

In a special embodiment of the invention, the method described herein is aimed at the detection of heat lysis resistant bacteria.

In a special embodiment of the invention, the method described herein is aimed for use with Mycobacteria.

In a special embodiment of the invention, the methods described herein are aimed for use with eukaryotic cells.

In a special embodiment of the invention, the method described herein is aimed for use with mammalian cells.

In a special embodiment of the invention, the method is for use with human cells, fungal cells, plant cells or with viruses.

In a special embodiment of the invention, the methods is for use in a capillary design where the cell or spore suspension is contained in-between two or more electrode surfaces.

In a special embodiment of the invention, the lysis is induced by the application of high frequency alternating fields.

In a special embodiment of the invention, the applied frequency of the high frequency alternating field is between 8000 and 200,000 Hz.

In a special embodiment of the invention, the alternating field is applied pulse sequences between 1 and 60 sec.

In a special embodiment of the invention, the method included the application of short breaks in-between pulses.

In a special embodiment of the invention, the applied voltages are between 6 and 40 V.

In a special embodiment of the invention, the method is performed on the cells or spores suspended in demineralized water.

In a special embodiment of the invention, the cells or spores are suspended in PCR buffer formulation.

In a special embodiment of the invention, the methods is for use in combination with a capture device.

In a special embodiment of the invention, the method is for use in combination with a spore capture device.

In a special embodiment of the invention, the method is for use in combination with a cell capture device.

In a special embodiment of the invention, the method is to be used in combination with an electrostatic capture device.

In a special embodiment of the invention, the electrostatic capture device is a part of an integrated spore capture and lysis design.

In a preferred embodiment of the invention, the method, chip, device and system are not for electroporation and/or fusion of biological cells.

It should be noted that, according to the present invention, embodiments and features described in the context of one of the aspects of the present invention also apply to the other aspects of the invention.

EXAMPLES

Example 1

DNA Quality Following the Application of an Alternating Electric Potential

Figure 2:
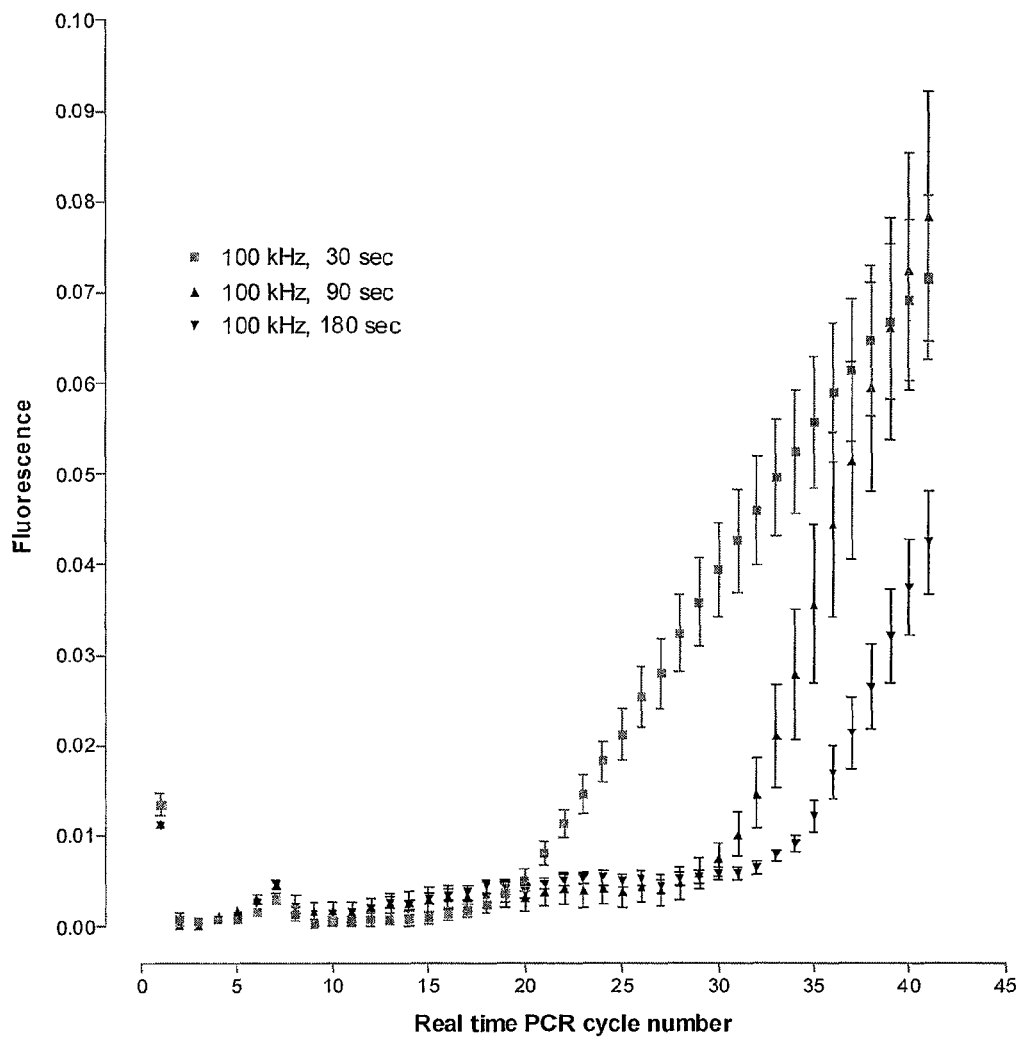
FIG. 2 shows the effect of prolonged exposure to the alternating electric field on the DNA/RNA release percentage (measured via real-time PCR and fluorescence)
Figure 3:
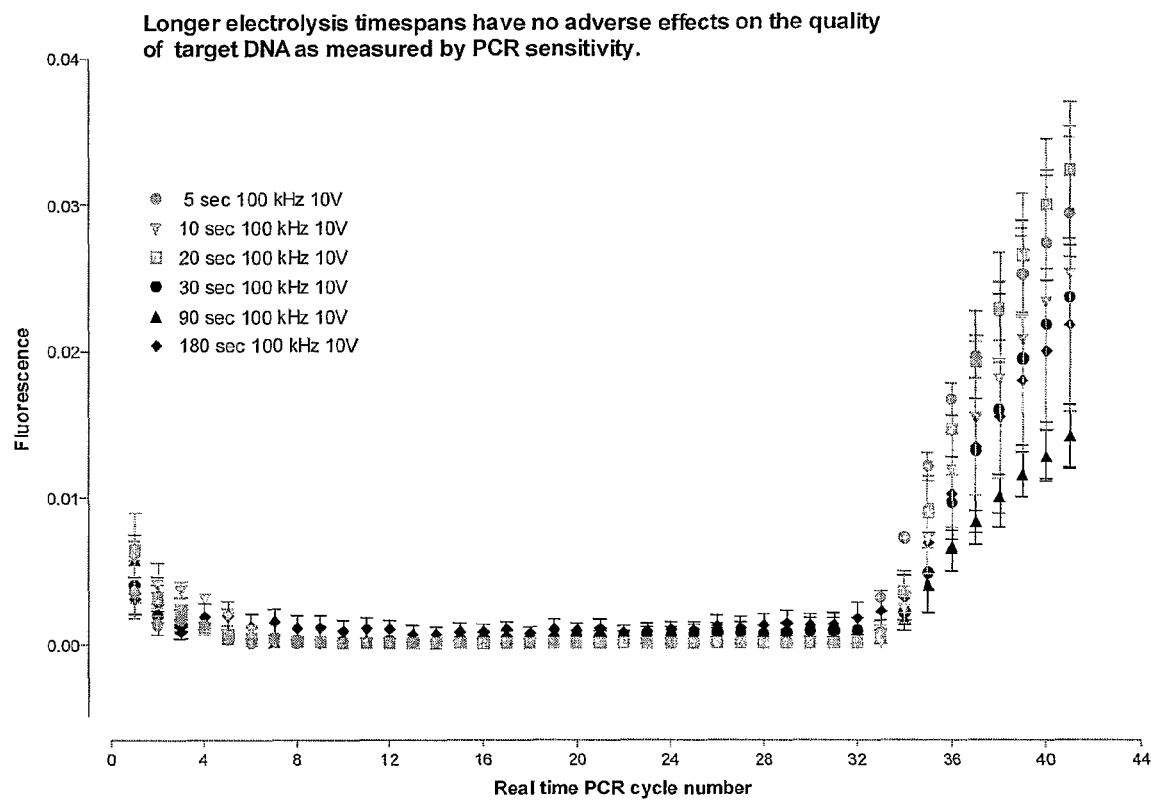
FIG. 3 shows that longer exposure times have no adverse effect on the quality of the target DNA.
Figure 4:
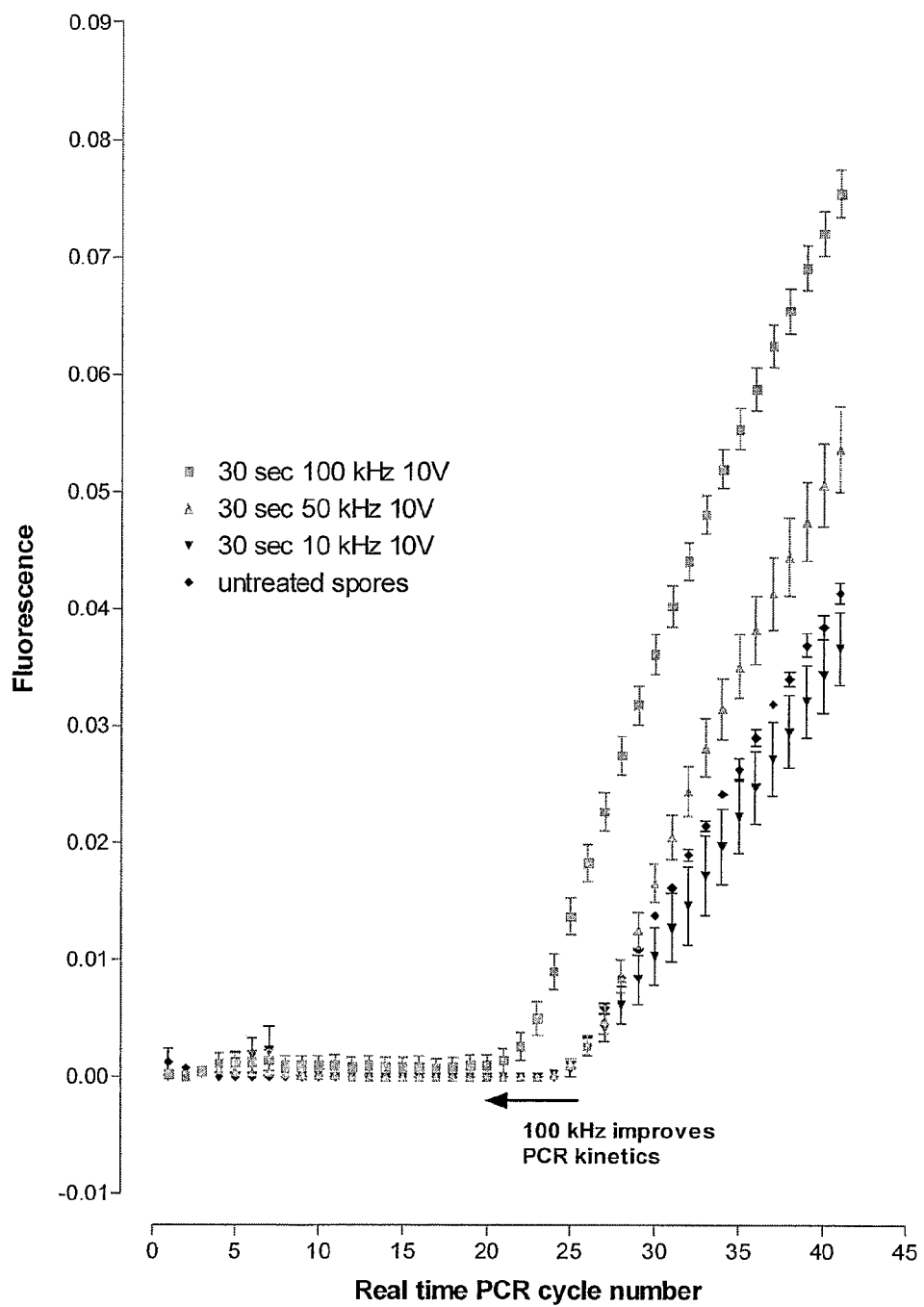
FIG. 4 shows the effect of the frequency of the alternating electric field on the DNA/RNA release percentage (measured via real-time PCR and fluorescence)
Figure 5:
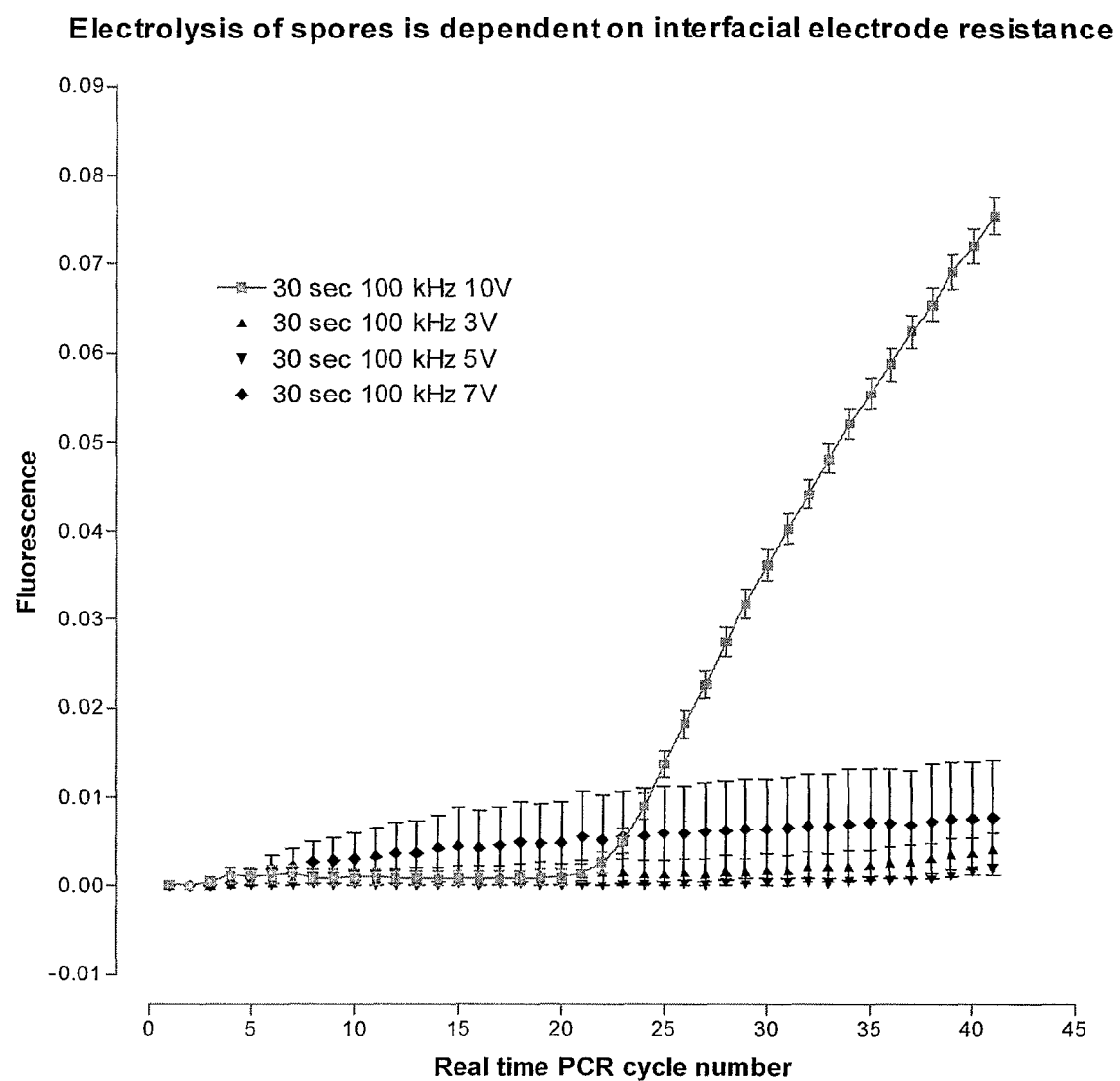
FIG. 5 shows the effect of the amplitude of the alternating electric field on the DNA/RNA release percentage (measured via real-time PCR and fluorescence)
Figure 6:
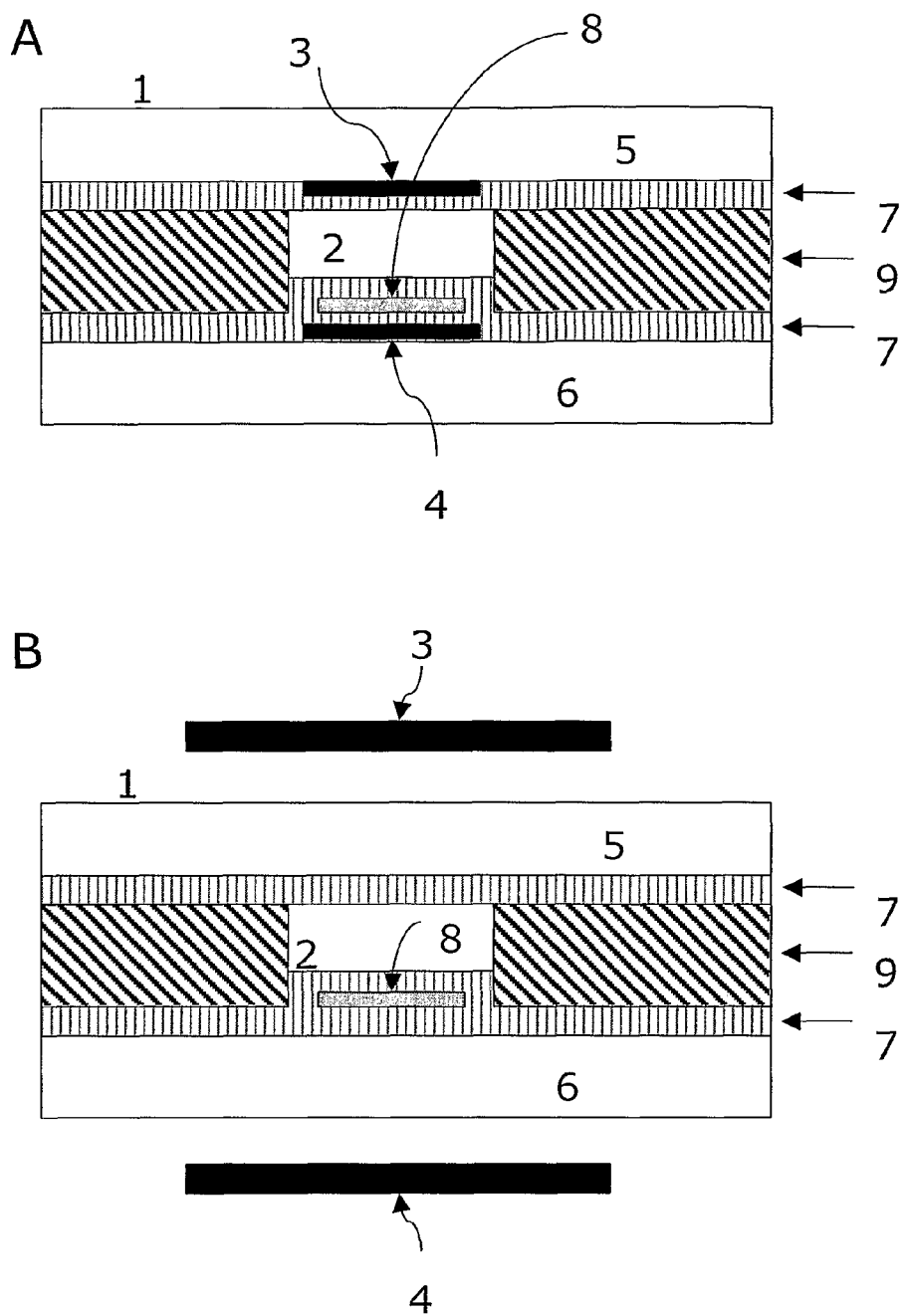
FIG. 6 shows the cross section of two embodiment of a chip.

Real-time PCR analysis was performed on an Opticon DNA engine (MJ research) using the TaqMan Universal PCR Master Mix system (Applied Biosystems), which is an integrated solution containing buffer, dNTP's and Taq polymerase. The two primers 269-16-23spacer1 5'-TAT GAG CTA CAC TGT TAT CTA GTT TTC AAA GAA-3' (SEQ ID NO 1) and 270-16-23spacer2 5'-TTT CCG TGT TTC GTT TTG TTC AG-3' (SEQ ID NO 2) were added at a final concentration of 900 nM and a fluorescent TAQMAN probe (FAM-ACT TCT CTC ATA TAT AAA TGT-MGB-NFQ) (SEQ ID NO 3) at 100 nM all aimed at amplifying the intergenetic spacer of the 16S and 23S tRNA genes of Bacillus thurigiensis. The standard PCR used a 15 µl sample volume and PCR was initiated by incubation 15 minutes at 95° C. to activate the Taq polymerase. Subsequently 40 cycles of a two step PCR reaction was applied being a 15 sec. melting step at 94° C. and a combined annealing and extension step of 60 sec. at 60° C. At the end of each cycle the fluorescence was measured on-line to analyze PCR product formation.

The chromosomal DNA from two ml (approximately $10^9$ cells/ml) of an overnight culture of *Bacillus thuringiensis* subsp. *kurstaki* was isolated using the method of Boe et al. (Boe et al 1989). The purified DNA was dissolved in 75 μl TE-buffer, meaning that a $10^{-6}$ dilution should contain DNA from approx. 27 cells/μl.

Four μl of a $10^{-6}$ dilution of the chromosomal DNA solution (equivalent to ~100 genome copies) was used to analyze the possible damaging effect of high frequency electrical fields on diluted DNA samples. The standard detection PCR was performed to probe the influence of the electrical field(s) applied. In details, 20 μl of a $10^{-6}$ dilution of *Bacillus thuringiensis* chromosomal DNA was submitted to a 10V, 100 kHz high frequency electrolysis field at 5, 10, 20, or 30 seconds. Subsequently, four μl (the equivalent of 100 copies of the chromosome) of the treated DNA was subjected to real-time PCR analysis. All samples subjected to the electrolysis conditions, were detected after 34 cycles of PCR, meaning that no loss of detection sensitivity was observed. The fact that all differently treated DNA samples are detected at the same $C_T$ point further indicates that chemical reduction or oxidation of nucleotides bases is of minor effect on the sensitivity of the detection PCR (See FIG. 1). However, increasing the duration of the electrolysis procedure even further, (30, 90, or 180 seconds) shows that electrolysis time does have an effect when prolonged procedures are applied (See FIG. 2). Electrolysis for more than 30 sec presumably results in the release and over-saturation of target DNA, subsequently giving poor PCR detection as measured by quantitative PCR.

Example 2

Spore Lysis Following the Application of an Alternating Electric Potential as Measured by Quantitative PCR One hundred mg of Biobit *Bacillus thuringiensis* subsp. *kurstaki* containing $3.2\times10^9$ spores/g (Valent BioSciences Corp, Libertyville, USA) was resuspended in 1 ml of demineralized water and centrifuged for 90 sec. at 12000 rpm. This procedure was repeated 4 times. The supernatant was discarded. The final solution contained approximately $3.2\times10^8$ spores. This solution was diluted to a final concentration of $3.2\times10^5$ spores/ml. and subsequently used for electrolysis and PCR.

Keeping the frequency and voltage constant (100 kHz and 10 V, respectively), the duration of the electrolysis procedure was examined using variations of exposure time—ranging from 5 to 30 seconds. As evident from FIG. 3, there is no noticeable effect on the $C_T$ value, demonstrating that lysis of the spores is virtually time-independent. However, increasing the duration of the electrolysis procedure even further (30, 90, and 180 seconds, respectively), shows that electrolysis time does have an effect when prolonged procedures are applied (See FIG. 4). Electrolysis for more than 30 sec presumably results in the release and over-saturation of target DNA, subsequently giving poor PCR detection.

Example 3

The Effects of Varying Frequencies (10-100 kHz) on Spore Electrolysis Efficiency One hundred mg of Biobit *Bacillus thuringiensis* subsp. *kurstaki* containing $3.2\times10^9$ spores/g (Valent BioSciences Corp, Libertyville, USA) was resuspended in 1 ml of demineralized water and centrifuged for 90 sec. at 12000 rpm. This procedure was repeated 4 times. The supernatant was discarded. The final solution contains approximately $3.2\times10^8$ spores. This solution was diluted to a final concentration of $3.2\times10^5$ spores/ml. and subsequently used for electrolysis and PCR.

Voltage and time were kept constant (at 10 V and 30 sec, respectively). FIG. 4 shows the results of this experiment and as apparent, the high frequency of 100 kHz showed a decrease in $C_T$ (threshold cycle), thus demonstrating release of amplifiable DNA from the spores. Lowering the frequency to 50 kHz or 10 kHz did not give rise to any improvement in the $C_T$ values (i.e. a lowering of $C_T$ compared to untreated controls).

Example 4

Determination of the Minimal Effective Voltage for Electrolysis of Spores

Keeping the frequency and time constant (100 kHz and 30 sec, respectively), the voltage of the electrolysis procedure was examined using variations of exposure voltage—ranging from 3 to 10 Volts (3, 5, 7, and 10 V, respectively). As evident from FIG. 5, it is apparent that a threshold voltage value $V_T$ for membrane/spore rupture exists. Thus, the applied voltage is a critical parameter highly dependent on the interfacial electrode resistance, e.g. a small, applied voltage (<2 V) gives a very small potential gradient across the electrodes even at long pulse times (>100 μs); a peak shaped gradient is created.

The maximum magnitude of applied voltage in solution can be calculated by convoluting exponential functions for the instrument rise time and charging time. For example, an instrument rise time of 8 μs and a charging time in the range 20-40 μs gives a maximum of 15-18% of the applied amplitude. The maximum is achieved approximately 10-15 μs after application of the pulse. After 50-75 μs the potential drop is effectively zero because all the applied voltage appears at the electrode-solution interface. At higher voltages the interfacial impedances becomes negligible and the current that passes between the electrodes is limited by the solution conductance.

Example 5

Determination of DNA/RNA Release Percentage

One hundred mg of Biobit *Bacillus thuringiensis* subsp. *kurstaki* containing approximately $10^9$ CFU/g (Valent BioSciences Corp, Libertyville, USA) are resuspended in 1 ml of demineralized water and subsequently pasteurised at 70° C. for 5 minutes, subsequently the solution is centrifuged (5000×g, 5 minutes). The supernatant is discarded—This (Tyndalisation) procedure is repeated two times more. The final 1 ml solution contains approximately $10^8$ spores.

This solution is diluted to a final concentration of $10^5$ spores/ml, thus constituting the stock solution.

The sample chamber is filled with a sample of stock solution and the sample is exposed to an alternating electric field having a selected frequency, amplitude, and duration.

To determine the DNA/RNA release percentage of the biological cells of the sample, both the exposed sample and a control containing stock solution is treated with the fluorochrome 4',6-diamidino-2-phenylindole (DAPI™). DAPI is widely used as a DNA stain that forms a fluorescent complex when bound to A-T rich sequences in the minor groove of dsDNA. The staining solution is an aqueous solution containing 2.0 μg/ml DAPI. Furthermore, DAPI has limited cell permeability and is therefore optimal for showing cellular release of genetic material.

The sample chamber is eluted with a volume of staining solution which volume is three times the volume of the sample chamber. The eluent from the sample chamber is allowed to incubate at room temperature for 5 minutes.

A volume of control comparable to volume of the exposed sample is stained separately for 5 minutes with a volume of staining solution being approximately three times the volume of the control.

Then an appropriate volume of the control and an appropriate volume of the exposed sample are then viewed in phase-contrast microscopy and fluorescence microscopy (supplied with a DAPI filter). For both the control and the exposed sample, the number of spores is counted by phase-contrast microscopy and the number of spores exhibiting a release chromosomal DNA molecules (visible as blue spots) is counted by fluorescence microscopy. The DNA/RNA release percentage is then determined as $$d_s/s_s\cdot 100\%$$

where $d_s$ is the counted number of blue DNA spots and $s_s$ is the total number of spores.

The background DNA/RNA release percentage may also determined for the control and if it shows an background release of more than 5%, it is suggested that the determination deemed invalid and that it is repeated on a new stock solution of biological cells.

REFERENCES

Levi et al. Levi, K., Higham, J. L., Coates, D., & Hamlyn, P. F. (2003) Molecular detection of anthrax spores on animal fibres. *Letters in Applied Microbiology* 36, 418-422.

Boe et al. Boe L, Gros M F, te Riele H, Ehrlich S D, Gruss A. (1989) Replication origins of single-stranded-DNA plasmid pUB110. *J Bacteriol.* 171(6):3366-72

Cano & Borucki Cano R J, Borucki M K. (1995). Revival and identification of bacterial spores in 25- to 40-million-year-old Dominican amber. *Science.* 268: 1060-4.

Johns et al. Johns, M., L. Harrington, R. W. Titball, and D. L. Leslie. (1994). Improved methods for the detection of *Bacillus anthracis* spores by the polymerase chain reaction. *Lett. Appl. Microbiol.* 18:236-238.

Linden, D. Linden, David. (1984). Handbook of Batteries and Fuel Cells. New York: McGraw-Hill.

The invention claimed is:

1. A method for extracting biological material from a bacterial spore, the method comprising the steps of:
   a) providing a sample chamber and a first and a second electrode, the first and the second electrode and the sample chamber being so positioned that at least a part of the sample chamber is between the first and the second electrode, said sample chamber having a volume of at most 500 μL,
   b) providing a liquid sample in the sample chamber, which liquid sample comprises a bacterial spore,
   c) exposing said liquid sample to an alternating electric field in said sample chamber, said alternating electric field being provided by the first and the second electrode and having a sufficient amplitude so as to extract biological material from the bacterial spore, and
   d) performing an analysis on a part of the exposed liquid sample, said part comprising extracted biological material from the bacterial spore.

2. The method according to claim 1, wherein the first and the second electrode are separated by a distance being at the most 20 mm.

3. The method according to claim 1, wherein the bacterial spore is either attached to and/or located between the first and the second electrode.

4. The method according to claim 1, wherein the frequency of the alternating electric field is at least 5 kHz.

5. The method according to claim 4, wherein the frequency of the alternating electric field is at the least 100 kHz.

6. The method according to claim 1, wherein the alternating electric field is created by modulating the polarity of the first and the second electrode.

7. The method according to claim 1, wherein the alternating electric field has a form chosen from the group consisting of: rectangular, sinusoidal, saw-tooth, asymmetrical triangular, symmetric triangular; or any combination thereof.

8. The method according to claim 1, wherein the alternating electric field, in the frequency domain, comprises at least a first and a second frequency component.

9. The method according to claim 1, wherein the biological material comprises a component selected from the group consisting of a cell organelle, a genetic material, and a protein.

10. The method according to claim 9, wherein the genetic material comprises chromosomal DNA and/or plasmid DNA and/or any type of RNA.

11. The method according to claim 9, wherein the protein is selected from the group consisting of enzymes, structural proteins, transport proteins, ion channels, toxins, hormones, and receptors.

12. The method according to claim 1, wherein the bacterial spore is selected from the genus *Bacillus* and/or the genus *Clostridium*.

13. The method according to claim 1, wherein the bacterial spore is from the *Bacillus* group.

14. The method according to claim 13, wherein the bacterial spore is *Bacillus anthracis*.

* * * * *